(12) United States Patent
Pelletier et al.

(10) Patent No.: US 9,234,835 B2
(45) Date of Patent: Jan. 12, 2016

(54) APPARATUS AND METHOD FOR ANALYSIS OF A FLUID SAMPLE

(75) Inventors: Michael T Pelletier, Houston, TX (US);
Gregory P Perez, Pearland, TX (US);
Christopher Michael Jones, Houston, TX (US); Gregory N Gilbert, Sugar Land, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 446 days.

(21) Appl. No.: 12/936,509

(22) PCT Filed: Apr. 7, 2009

(86) PCT No.: PCT/US2009/039788
§ 371 (c)(1),
(2), (4) Date: Oct. 5, 2010

(87) PCT Pub. No.: WO2009/126636
PCT Pub. Date: Oct. 15, 2009

(65) Prior Publication Data
US 2011/0023594 A1    Feb. 3, 2011

Related U.S. Application Data

(60) Provisional application No. 61/043,453, filed on Apr. 9, 2008.

(51) Int. Cl.
*G01N 29/42* (2006.01)
*G01N 21/17* (2006.01)
*G01N 29/24* (2006.01)

(52) U.S. Cl.
CPC ........ *G01N 21/1702* (2013.01); *G01N 29/2418* (2013.01); *G01N 29/42* (2013.01); *G01N 2021/1727* (2013.01); *G01N 2021/1761* (2013.01)

(58) Field of Classification Search
USPC ............... 73/152.18, 152.23–152.28, 152.42, 73/24.01, 24.02
See application file for complete search history.

(56) References Cited

U.S. PATENT DOCUMENTS

| 5,159,411 A | * | 10/1992 | Hammerich et al. ......... 356/432 |
| 5,184,508 A | | 2/1993 | Desbrandes |
| 5,348,002 A | * | 9/1994 | Caro ............................. 600/310 |

(Continued)

FOREIGN PATENT DOCUMENTS

| GB | 2407109 | 4/2005 |
| WO | 2006063094 | 6/2006 |

OTHER PUBLICATIONS

David A Walls, Lenny Shaver, The Latest Advancements in Photoacoustic Spectroscopy (PAS) for Gas Analysis and Monitoring, Presentation, Apr. 17, 2007.

(Continued)

*Primary Examiner* — John Fitzgerald
(74) *Attorney, Agent, or Firm* — McGuireWoods, LLP (57) ABSTRACT

An apparatus for analyzing a fluid comprises a chamber to receive a fluid sample. A pump reduces a pressure in the chamber below a vapor pressure of a component of the fluid sample. At least one light system provides a light at a predetermined modulation frequency to the fluid sample. An acoustic sensor detects an acoustic signal caused by the interaction of the light and the fluid sample. A controller relates the acoustic signal to at least one chemical component of the fluid sample.

13 Claims, 5 Drawing Sheets

(56) References Cited

U.S. PATENT DOCUMENTS

| | | | |
|---|---|---|---|
| 5,447,052 A * | 9/1995 | Delaune et al. | 73/19.09 |
| 5,602,334 A | 2/1997 | Proett et al. | |
| 5,644,076 A | 7/1997 | Proett et al. | |
| 6,218,662 B1 | 4/2001 | Tchakarov et al. | |
| 6,939,717 B2 * | 9/2005 | Jiang et al. | 436/121 |
| 7,095,012 B2 * | 8/2006 | Fujisawa et al. | 250/269.1 |
| 7,100,689 B2 * | 9/2006 | Williams et al. | 166/264 |
| 7,191,672 B2 * | 3/2007 | Ringgenberg et al. | 73/864.61 |
| 7,222,524 B2 * | 5/2007 | Shammai | 73/152.24 |
| 7,318,343 B2 * | 1/2008 | Coenen | 73/152.19 |
| 7,362,422 B2 * | 4/2008 | DiFoggio et al. | 356/70 |
| 7,387,021 B2 * | 6/2008 | DiFoggio | 73/152.55 |
| 7,423,258 B2 * | 9/2008 | DiFoggio et al. | 250/269.1 |
| 7,511,819 B2 * | 3/2009 | DiFoggio | 356/436 |
| 7,516,655 B2 * | 4/2009 | DiFoggio | 73/152.58 |
| 7,520,158 B2 * | 4/2009 | DiFoggio | 73/19.1 |
| 7,781,737 B2 * | 8/2010 | Zhdaneev | 250/339.08 |
| 7,804,598 B2 * | 9/2010 | Hall et al. | 356/445 |
| 7,828,058 B2 * | 11/2010 | Fielder | 166/250.15 |
| 7,921,693 B2 * | 4/2011 | Van Herpen | 73/24.02 |
| 8,037,747 B2 * | 10/2011 | DiFoggio | 73/152.23 |
| 2002/0178782 A1 | 12/2002 | Lange et al. | |
| 2003/0134426 A1 * | 7/2003 | Jiang et al. | 436/121 |
| 2004/0159149 A1 * | 8/2004 | Williams et al. | 73/152.23 |
| 2005/0099618 A1 * | 5/2005 | DiFoggio et al. | 356/70 |
| 2005/0241382 A1 * | 11/2005 | Coenen | 73/152.19 |
| 2006/0175547 A1 * | 8/2006 | DiFoggio et al. | 250/269.1 |
| 2006/0266108 A1 | 11/2006 | DiFoggio | |
| 2006/0266109 A1 | 11/2006 | DiFoggio | |
| 2007/0013911 A1 * | 1/2007 | DiFoggio | 356/436 |
| 2007/0035736 A1 | 2/2007 | Vannuffelen et al. | |
| 2007/0119244 A1 | 5/2007 | Goodwin et al. | |
| 2007/0137293 A1 * | 6/2007 | Pop et al. | 73/152.23 |
| 2007/0227241 A1 * | 10/2007 | DiFoggio | 73/152.23 |
| 2008/0121016 A1 * | 5/2008 | Shah et al. | 73/23.42 |
| 2008/0149819 A1 * | 6/2008 | Zhdaneev | 250/255 |
| 2009/0158820 A1 * | 6/2009 | Bostrom et al. | 73/61.53 |
| 2011/0016962 A1 * | 1/2011 | DiFoggio | 73/152.15 |

OTHER PUBLICATIONS

Measuring Gases with the Help of Microphones—Photoacoustic Effect, Report, InnovaAirtech A/S, 2005.

C. Haisch, R. Niessner, Light and Sound—Photoacoustic Spectroscopy, Magazine article, Spectroscopy Europe, 14/5, 2002, pp. 10-15.

* cited by examiner

APPARATUS AND METHOD FOR ANALYSIS OF A FLUID SAMPLE

BACKGROUND OF THE INVENTION

The present invention relates generally to the determination of the composition of a fluid sample. More specifically, the present invention relates to the determination of the composition of a multi-component fluid using detected acoustical signals related to the various components of the fluid sample.

It is of interest to know the both composition and concentration of materials in a fluid extracted from a reservoir or a fluid stream. In the case of reservoirs, the analysis may comprise extracting fluid from the native formation by pumping with a formation test tool, flowing the well in a drill stem test or examining the drill cuttings circulated to surface during drilling. The examination of the samples may be accomplished by transporting a quantity of the fluids to a laboratory and the separating the fluid into its constituent parts by distillation and/or by chromatographic methods. Another method relies on the measurement of light transmitted through a sample. This approach places a windowed cell within the fluid flow path of a formation testing tool. In one example, this method may require the determination of the amount of power delivered to the sample and the amount of power that is transmitted through the sample. The care and maintenance of the optical receiver can be difficult. High downhole temperatures can adversely effect a photodiode used as a receiver.

BRIEF DESCRIPTION OF THE DRAWINGS

A better understanding of the present invention can be obtained when the following detailed description of example embodiments are considered in conjunction with the following drawings, in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention as defined by the appended claims.

DETAILED DESCRIPTION

Photoacoustic spectroscopy (PAS) is based on the absorption of light energy by a molecule. The signal in PAS is monitored by acoustic detection. Photoacoustic spectroscopic detection is based on the generation of acoustic waves as a consequence of light absorption. Absorption of light by a sample exposed thereto excites molecules in the sample. Modulation of the light intensity (turning the light on and off as the sample is exposed) causes the temperature of the sample to rise and fall with the absorption profile of the sample. As used herein, light refers to electromagnetic radiation of all wavelengths, whether visible or not. The temperature variation of the sample is accompanied by a pressure variation that creates a sound wave. The sound wave can be detected with an acoustic detector, for example a microphone. Many of the components of oil reservoir fluids have absorption bands in the infrared portion of the electromagnetic spectrum. By exciting the component with energy having a wavelength in the appropriate absorption band, the component can be caused to generate a sound signal which is indicative of the component. For gases, many of the absorption wavelengths are in the infrared portion of the electromagnetic spectrum. For example, the absorption wavelengths for hydrocarbon gases including methane, propane, and butane are in the range of 1677 nm and 1725 nm. Hydrogen sulfide gas has a group of absorption wavelengths near 1578 nm and carbon dioxide has several absorption wavelengths near 2007 nm and 1572 nm. It is to be noted that liquids may exhibit photoacoustic signal generation similar to, but possibly smaller in amplitude to, that of gases.

Figure 1:
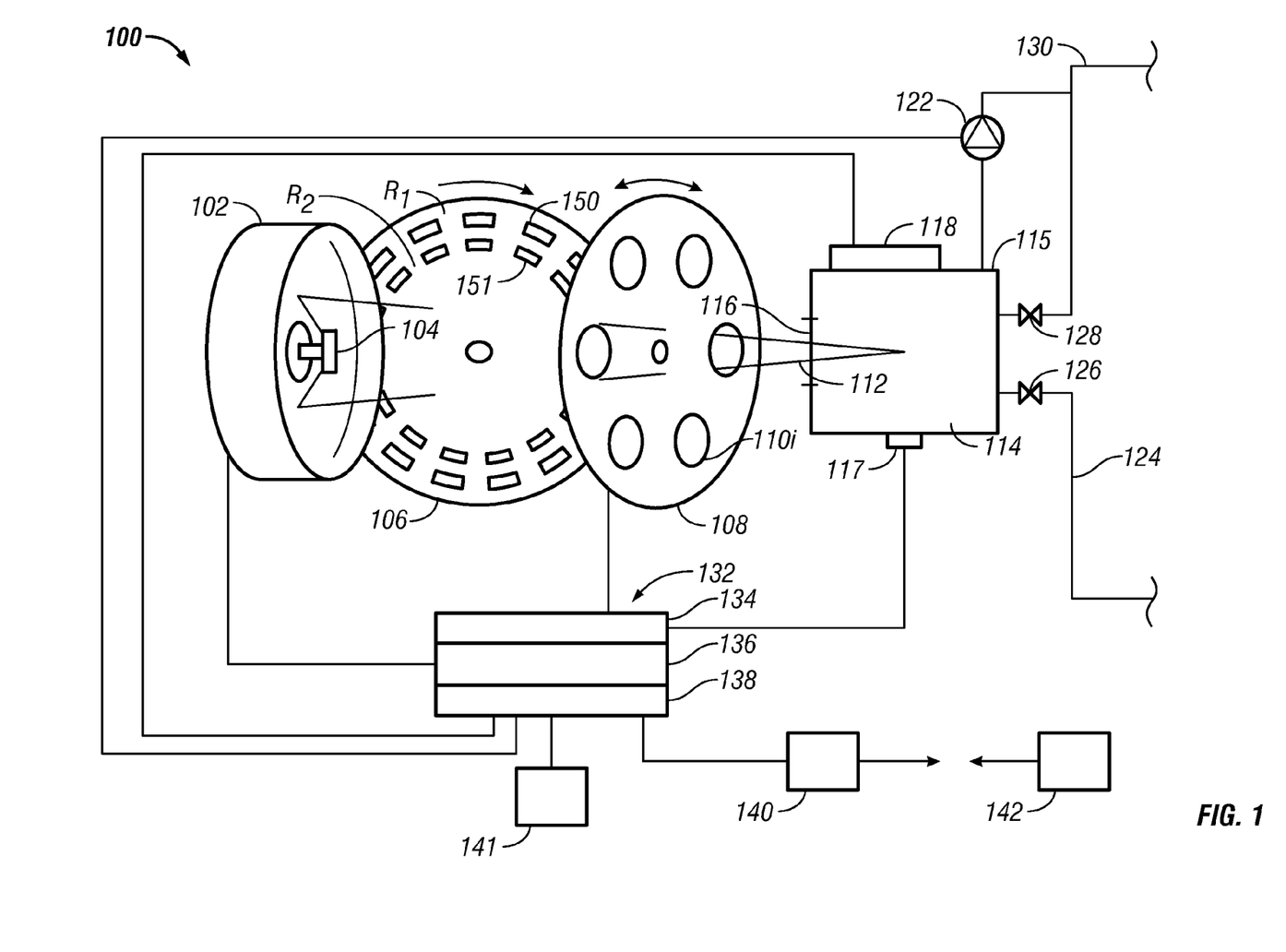
FIG. 1 shows a schematic of one example of a fluid analysis apparatus.

FIG. 1 shows a schematic of one example of an analysis apparatus 100 for determining the components of a fluid sample. As used herein, the term fluid is used to mean a gas, a liquid, and a combination of a gas and a liquid. In the example of FIG. 1, a fluid flowing in inlet line 124 is admitted to sample chamber 115 through valve 126. and sealed off by closing valves 126 and 128. Sample chamber 115 comprises an optical window 116 through at least a portion of one wall of sample chamber 115. Acoustic detector 117 may be inserted through the wall of sample chamber 115 and contact sample fluid 114. Acoustic detector 117 may comprise a capacitance microphone, a piezoelectric sensor, or any other suitable acoustic signal detector. Pump 122 is connected to sample chamber 115. In one embodiment pump 122 is a positive displacement pump. Positive displacement pumps include, but are not limited to, gear pumps and piston pumps. In one example, pump 122 may be activated to lower the pressure in sample chamber 115 below the vapor pressure of the fluid components such that substantially all of the original sample is converted to a gas phase. Pump 122 may also be used to pressure tune the acoustic response for enhanced signal generation. In one example, heater 118 may be attached to sample chamber 115 to raise the temperature of sample chamber 115 and sample 114 to assist in converting any liquid in sample chamber 115 to a gas phase. In another example. temperature may be used to pressure tune the photo acoustic response. In yet another example, the combination of a temperature tunable phase change substance with a temperature controlled cold element, both in operative contact with sample chamber 115, may be used to pressure tune the photo acoustic response. In one embodiment, the photo acoustic response of the phase change substance may serve as an internal reference standard.

In one embodiment, a light system 101 comprises light source 104, mirror 102, chopper wheel 106, and filter wheel 108. In one example, light source 104 may be a broad band infra-red source such as a heated filament wire. The energy from light source 104 may be collected and reflected by mirror 102 toward sample chamber 115. In one example, a focusing element (not shown) may be used to localize the energy within the sample 114 such that the intensity of the interaction is sufficient to generate a large temperature differential with respect to the surrounding fluid thereby allowing a large pressure gradient to form. The amplitude of the generated acoustic signal is related to the generated pressure gradient.

A motor (not shown) may drive chopper wheel 106 at a predetermined rate to modulate the light passed to sample 114 at a predetermined frequency, f. Rings $R_1$ and $R_2$ of slots 150 and 151 may be formed in chopper wheel 106. The length and spacing of the slots in each individual ring may be different, such that the duty cycle (frequency and duration) of the energy transmitted to heat the sample fluid 114 may be different through slots 150 as compared to the energy transmitted to heat the sample fluid 114 through slots 151. Any suitable number of rings Ri may be formed in chopper wheel 106. The sample is heated by the absorption of the energy from light source 104 during the exposed time. In contrast, when chopping wheel 106 block the energy, the sample 114 cools off. A filter wheel 108 may comprise several filters $110_i$ that allow passage of a predetermined wavelength $\lambda_i$ of the energy from source 104 that interacts with a component $C_i$ of sample 114. Alternatively, an electronic or mechanical shutter, or series of shutters, may be used instead of a chopper wheel. The heating and cooling of sample 114 generates pressure fluctuations that are related to the presence of component $C_i$ in sample 114. In one example, see FIG. 1, filter wheel 108 is rotatable such that one filter component $110_i$ is optically aligned to allow energy of wavelength $\lambda_i$ to interact with sample 114 at a first time interval. Filter wheel 108 may then turned to allow a different $\lambda_i$ to interact with sample 114 at a second time interval.

Figure 5:
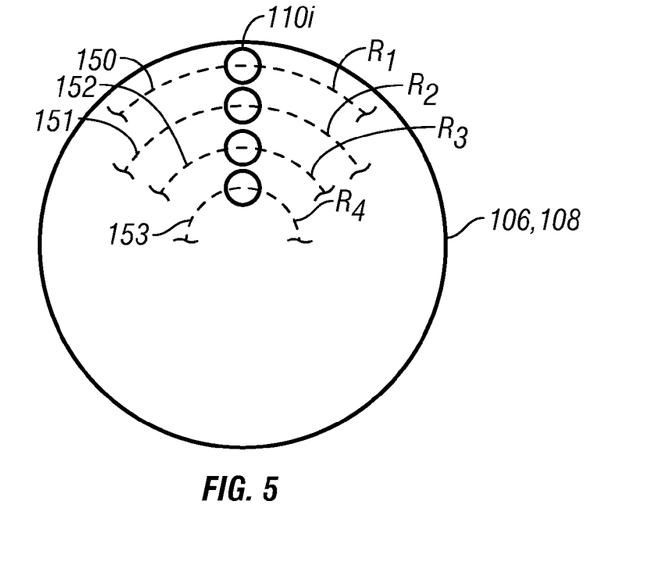
FIG. 5 shows one example of the overlapping relationship of a chopper wheel and a filter arrangement.

In another example, see FIG. 5, filter wheel 508 is shown overlaying chopper wheel 106. Filters $110_i$ may be arranged radially such that each filter passes a different characteristic wavelength, $\lambda_i$, interacting with a different ring Ri of slots 150-153. Energy may be transmitted from all of the filters simultaneously to sample 114. The heating and cooling from each ring of slots will have a characteristic frequency, $f_i$, related to the number and spacing of the slots in each ring, and the rotational speed of the chopper wheel. The various energy absorbing components of sample 114 will emit multiple acoustic frequencies related to the appropriate filter and slot interaction. Multiple components $C_i$ can be simultaneously identified. For example, energy of wavelengths $\lambda_1$ and $\lambda_2$, associated with rings $R_1$ and $R_2$, may be transmitted at frequencies $f_1$ and $f_2$ to interact with sample 114. Frequencies $f_1$ and $f_2$ are determined by the number of slots in rings $R_1$ and $R_2$ and the rotational rate of the chopper wheel 106. If sample 114 contains components $C_1$ and $C_2$, associated with wavelengths $\lambda_1$ and $\lambda_2$, the sample 114 will emit acoustic signals at frequencies $f_1$ and $f_2$. If, in another example, only component $C_1$ is present, then sample 114 will emit an acoustic signal at frequency $f_1$, but not at frequency $f_2$.

Controller 132 may comprise electronic circuits 134, a processor 136, and a memory 138 in data communication with processor 136. Electronic circuits 134 may interface with and supply power to light source 104, heater 118, acoustic detector 117, and pump 122. Processor 136 may comprise a single processor or multiple processors, including a digital signal processor. Programmed instructions may be stored in memory 138 that when executed by processor 136, controls the operation of analysis apparatus 100. In one example, electronic circuits 134 may comprise analog filters to detect signals at the predetermined frequencies discussed previously. Alternatively, the sensor signal may be digitized and analyzed digitally for signals at the predetermined frequencies using techniques known in the art. In addition, data and models may be stored in memory 138 that relates the acoustic signal to the components $C_i$. For example, data relating to the specific absorption wavelengths may be stored in memory 138 for use in identifying the components of sample 114. In one example, data may be transmitted from controller 132 by telemetry device 140 to an external controller 142 for further data analysis and correlation. Alternatively, data may be stored on a computer readable medium 141 that may comprise a hard disk, a flash memory, a CD, a DVD, or any other suitable computer readable medium.

Figure 2:
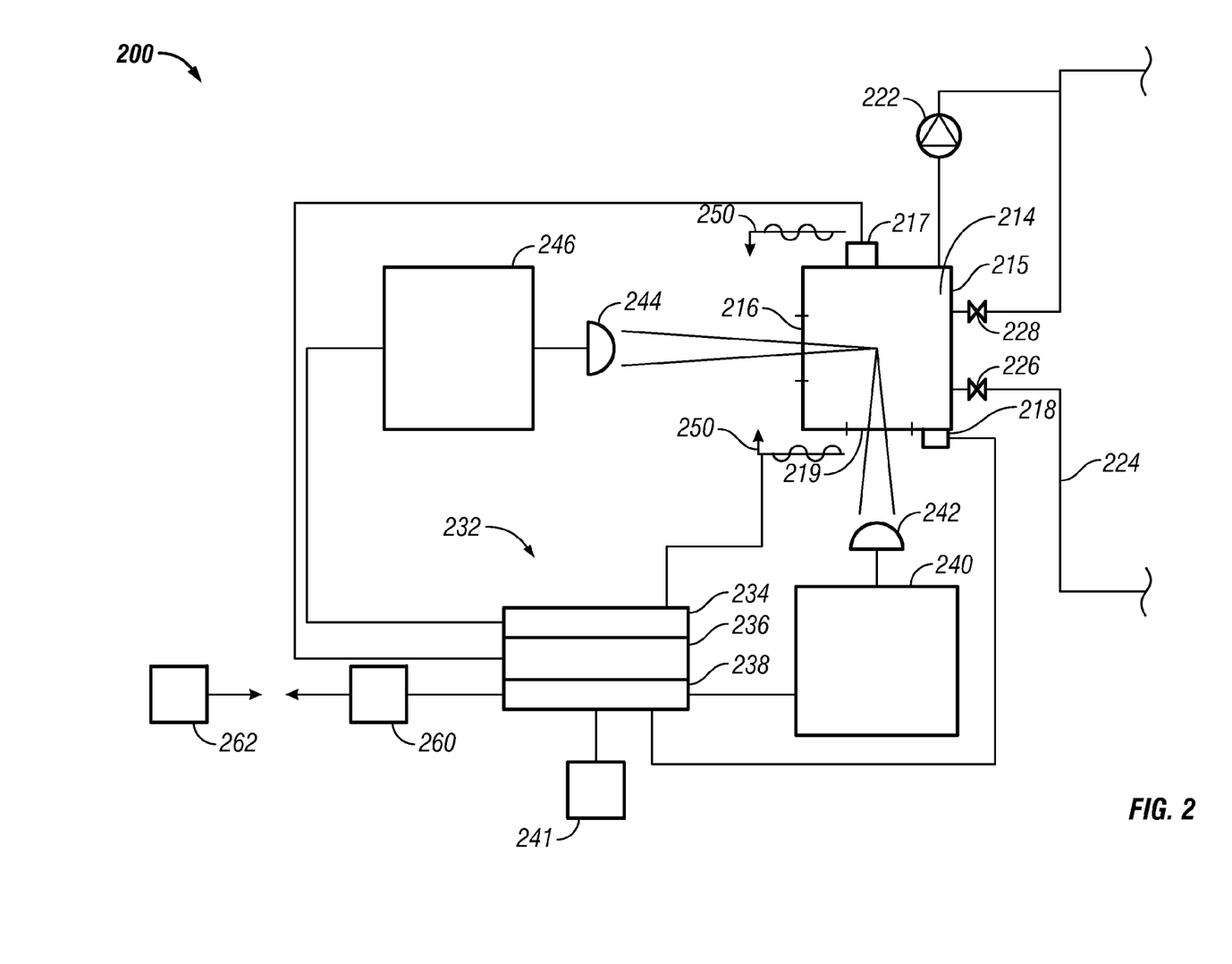
FIG. 2 shows a schematic of another example of a fluid analysis apparatus.

In another embodiment, FIG. 2 shows a schematic of one example of an analysis apparatus 200 for determining the components of a fluid sample. A fluid flowing in inlet line 224 is admitted to sample chamber 215 through valve 226, and sealed off by closing valves 226 and 228. Sample chamber 215 may comprise optical windows 216 and 219 through the walls of sample chamber 215. Acoustic detector 217 may be inserted through the wall of sample chamber 215 and contacts sample fluid 214. Pump 222 is connected to sample chamber 215. Pump 222 may be a positive displacement pump similar to pump 122 of FIG. 1. Positive displacement pumps include, but are not limited to, gear pumps and piston pumps. Pump 222 may be activated to lower the pressure in sample chamber 215 such that substantially all of the original sample is converted to a gas phase. Alternatively, an aliquot of the sample may be introduced into the chamber at reduced pressure with higher, the same, or lower temperature than the original fluid in order to flash the sample to the gas phase. In one example, heater 218 may be attached to sample chamber 215 to raise the temperature of sample chamber 215 and sample 214 to assist in converting any liquid in sample chamber 215 to a gas phase.

Light sources 244 and 242 may be narrow band infrared sources such as a laser, a laser diode, and a tunable laser diode. Each light source may emit a different light wavelength $\lambda_i$ for identifying different components $C_i$ of sample 214. While shown with two optical energy sources, it is understood that any number of light sources may be employed within the constraints of providing a suitable window access to sample 214. Alternatively, optical fibers may be placed and sealed through the wall. In one example, energy may be introduced to the sample using nanofiber evanescent field generation, known in the art.

Source controllers 246 and 240 may comprise control circuits for controlling the activation of sources 244 and 242 respectively. For example, such circuits may control the on-off frequency and amplitude of each source. This capability allows these types of sources to operate without the need for the mechanical chopper and the filter wheel of the embodiment shown in FIG. 1. The heating and cooling of sample 214 generates pressure fluctuations that are related to the presence of component $C_i$ in sample 214. Controller 232 may comprise electronic circuits 234, a processor 236, and a memory 238 in data communication with processor 236. Electronic circuits 234 may interface with and supply power to controller sources 246 and 240, heater 218, acoustic detector 217, and pump 222. The sources 242 and 244 may be operated simultaneously, at different duty cycles, for simultaneous detection of components $C_i$ of sample 214. The electronic control of the sources allows controller 232 to synchronize the signal detection to the source activation to enhance the signal to noise ratio. Processor 236 may comprise a single processor or multiple processors, including a digital signal processor. Programmed instructions may be stored in memory 238 that when executed by processor 236, controls the operation of analysis apparatus 200. In addition, data and models may be stored in memory 238 that relates the acoustic signal to the components $C_i$. For example, data relating to the specific absorption frequencies may be stored in memory 238 for use in identifying the components of sample 214. Alternatively, data may be stored on a computer readable medium 241 that may comprise a hard disk, a flash memory, a CD, a DVD, or any other suitable computer readable medium.

In one example, still referring to FIG. 2, an electromagnet 250 may be disposed at least partially around sample chamber 215 for use in detecting oxygen, $O_2$, in sample 214. Oxygen does not absorb infrared light. However, by subjecting sample 214 to a pulsating magnetic field, the oxygen molecules will start to vibrate generating a pressure change that is detected by acoustic detector 217. One skilled in the art will appreciate that a magnetic coil may also be incorporated around sample chamber 115 of FIG. 1.

Figure 3:
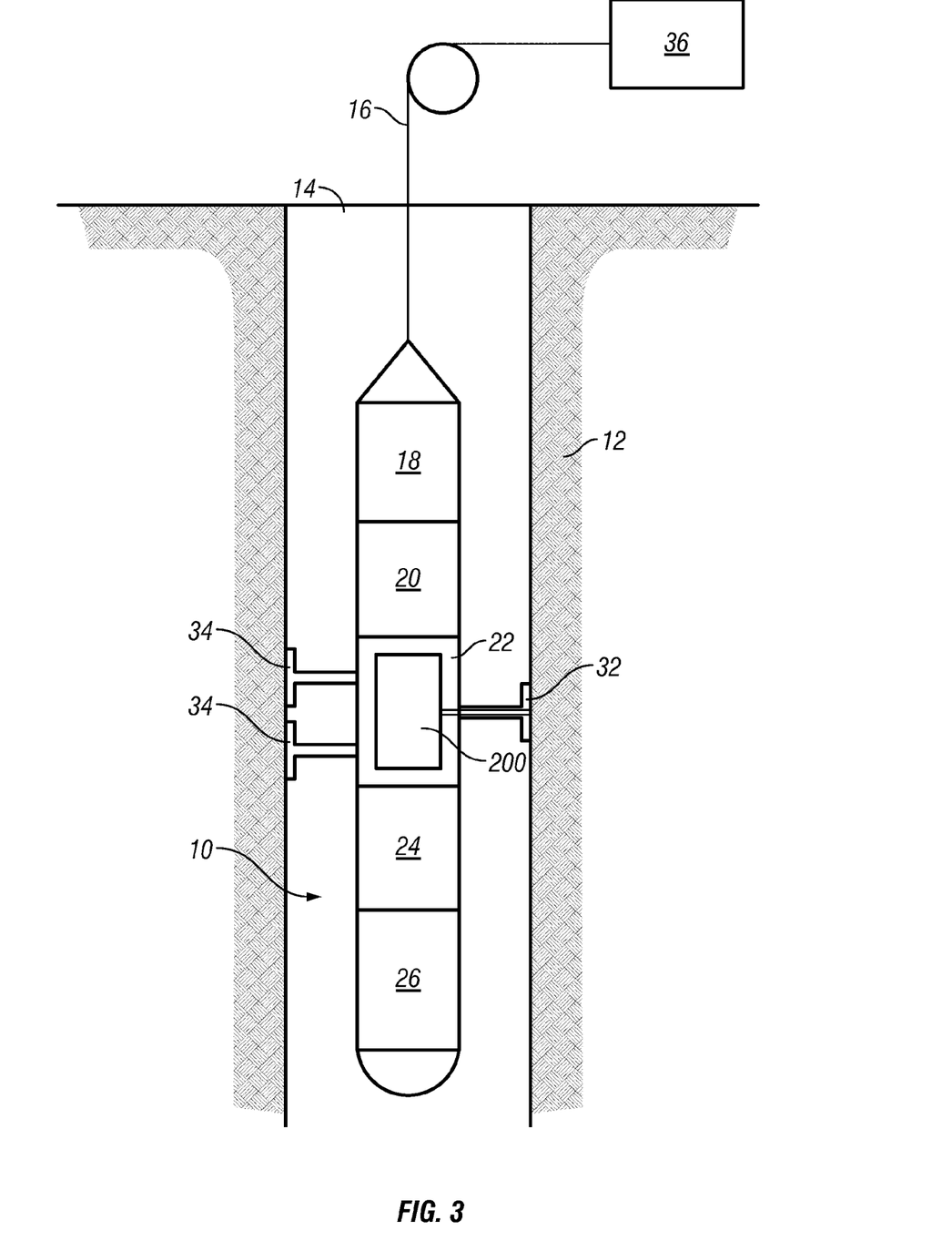
FIG. 3 is a partial sectional view of a formation testing tool having a fluid analysis apparatus.

In one example, FIG. 3 shows a formation testing tool 10 for obtaining and analyzing a fluid sample from a subterranean formation 12 through a wellbore 14. Formation testing tool 10 is suspended in wellbore 14 by a wireline cable 16 that connects the tool 10 to a surface control unit 36. Alternatively, formation testing tool 10 may be deployed in wellbore 14 on coiled tubing, jointed drill pipe, hard wired drill pipe, or any other suitable deployment technique. Formation testing tool 10 may comprise an elongated, cylindrical body 18 having a control module 20, fluid acquisition module 22, and fluid storage modules 24, 26. Fluid acquisition module 22 comprises an extendable fluid admitting probe 32 and extendable tool anchors 34. Fluid is drawn into the tool through probe 32 by a fluid pumping unit (not shown). The acquired fluid then flows through fluid measurement module 200 that, as described above, analyzes the fluid using PAS techniques described herein, and sends data to surface control unit 36 via the wireline cable 16. The fluid then can be stored in the fluid storage modules 24, 26 and retrieved to the surface for further analysis.

Figure 6:
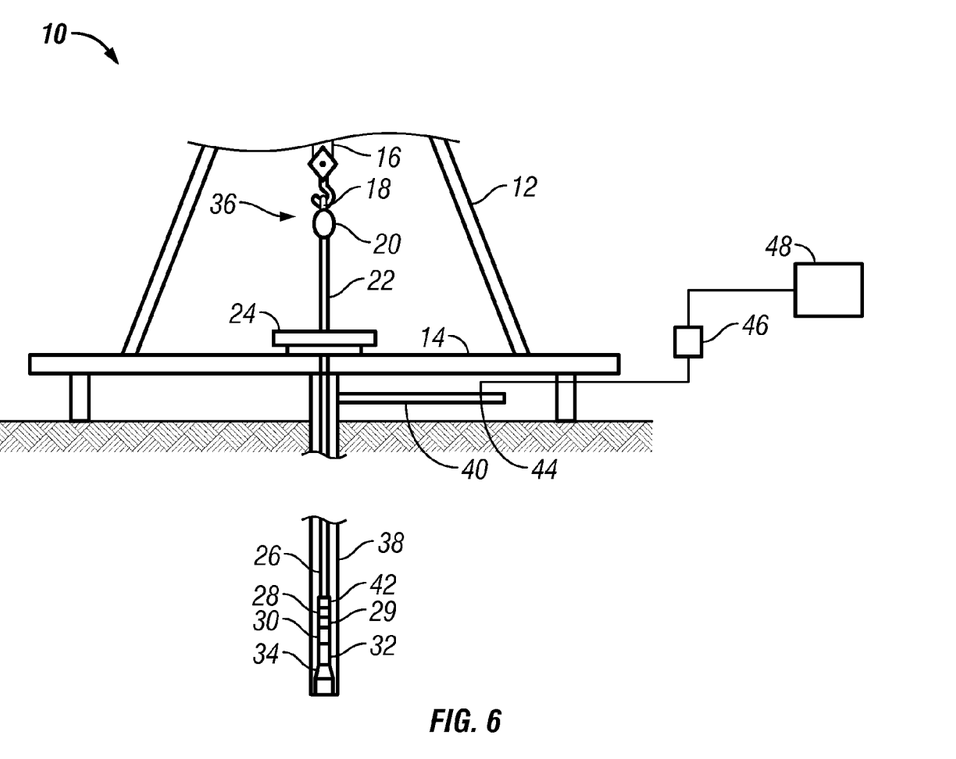
FIG. 6 shows a well drilling system comprising a bottom hole assembly that includes a formation testing tool.

In another example embodiment, referring to FIG. 6, a drilling rig 10 (simplified to exclude items not important to this application) comprises a derrick 12, derrick floor 14, draw works 16, hook 18, swivel 20, kelly joint 22 and rotary table 24, such components being arranged in a conventional manner so as to support and impart rotation to drillstring 26. Drill string 26 includes at its lower end a bottom hole assembly 29 which comprises drill collar 28, MWD tool 30 (which may be any kind of MWD tool, such as an acoustic logging tool), MWD formation testing tool 32 (which may be a separate tool as shown or may be incorporated into another tool) and drill bit 34. Drilling fluid (which may also be referred to as "drilling mud") is injected into the swivel by a mud supply line 36. The mud travels through the kelly joint 22, drillstring 26, drill collars 28, MWD tool 30 and MWD formation testing tool 32 and exits through ports in the drill bit 34. The mud then flows up the borehole 38. A mud return line 40 returns mud from the borehole 38 and circulates it to a mud pit (not shown) and ultimately back to the mud supply line 36.

The data collected by the MWD tool 30 and formation testing tool 32 may be returned to the surface for analysis by telemetry transmitted in any conventional manner, including but not limited to mud pulse telemetry, electromagnetic telemetry, and acoustic telemetry. Alternatively, drill string 26 and drill collars 28 may be hard wired to provide high data rate telemetry. For purposes of the present application, the embodiment described herein will be explained with respect to use of mud pulse telemetry. A telemetry transmitter 42 located in a drill collar 28 or in one of the MWD tools collects data from the MWD tools and transmits it through the mud via pressure pulses generated in the drilling mud. A telemetry sensor 44 on the surface detects the telemetry and returns it to a demodulator 46. The demodulator 46 demodulates the data and provides it to computing equipment 48 where the data is analyzed to extract useful geological information.

Further, commands may be passed downhole to the MWD tool and formation testing tool 32 in a variety of ways. In addition to the methods described in the previous paragraph, information may be transmitted by performing predefined sequences of drill pipe rotations that can be sensed in the MWD tools and translated into commands. Similarly, the mud pumps may be cycled on and off in predefined sequences to transmit information in a similar fashion.

Figure 7:
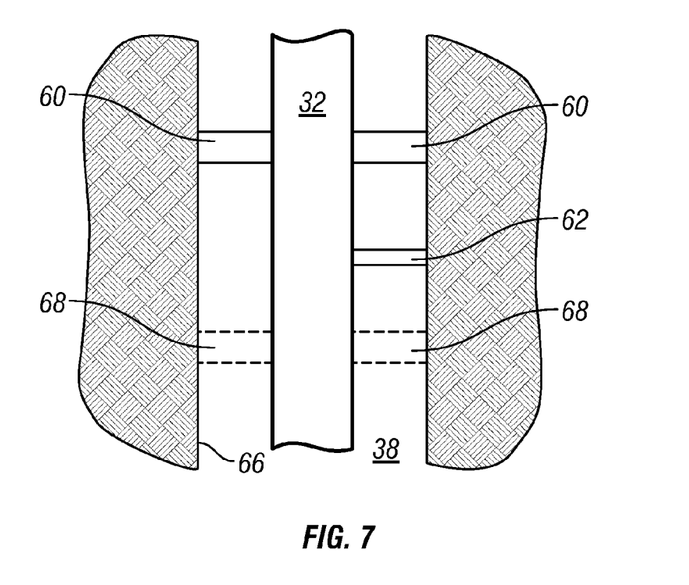
FIG. 7 shows an enlarged view of the formation testing tool of FIG. 6.

In one embodiment, the formation testing tool 32 comprises a plurality of centralizing pistons 60 and one or more sampling pistons 62, as shown in FIG. 7. For present purposes, the formation testing tool will be described with reference to tool 32 having one sampling piston 62, it being understood that the tool could likewise be configured to include additional such pistons 62. The plurality of centralizing pistons 60 centralize the formation testing tool 32 in the borehole 38. Once the formation testing tool 32 is centralized, the sampling piston 62 extends from the formation testing tool 32 to the borehole wall 66, where it seals against the wall and allows formation testing to be performed.

In one embodiment of the formation testing tool 32, the centralizing pistons 60 are all in the same cross section and the sampling piston 62 is in a different cross section. In another embodiment, one or more of the centralizing pistons 68 are in a different cross-section from the remaining centralizing pistons 60. In still another embodiment, the centralizing pistons are in three or more cross sections.

During drilling operations, the centralizing pistons 60 and the sampling piston 62 are retained in a retracted position inside the formation testing tool 32. In this position, the sampling piston 62 is recessed below the surface of the formation testing tool 32, as is discussed further below. When it is time to perform the formation testing function, the rotation of the drill string 26 is ceased and the centralizing pistons 60 are extended at the same rate so that the formation testing tool 32 is relatively centralized within the borehole, as shown in FIG. 7. The sampling piston 62 is then extended and the formation testing tool 32 performs its testing function, including analyzing the formation fluid using the PAS techniques described herein. One skilled in the art will appreciate that the above described MWD formation testing tool may be alternatively deployed in the wellbore with coiled tubing equipment (not shown), using techniques known in the art.

Figure 4:
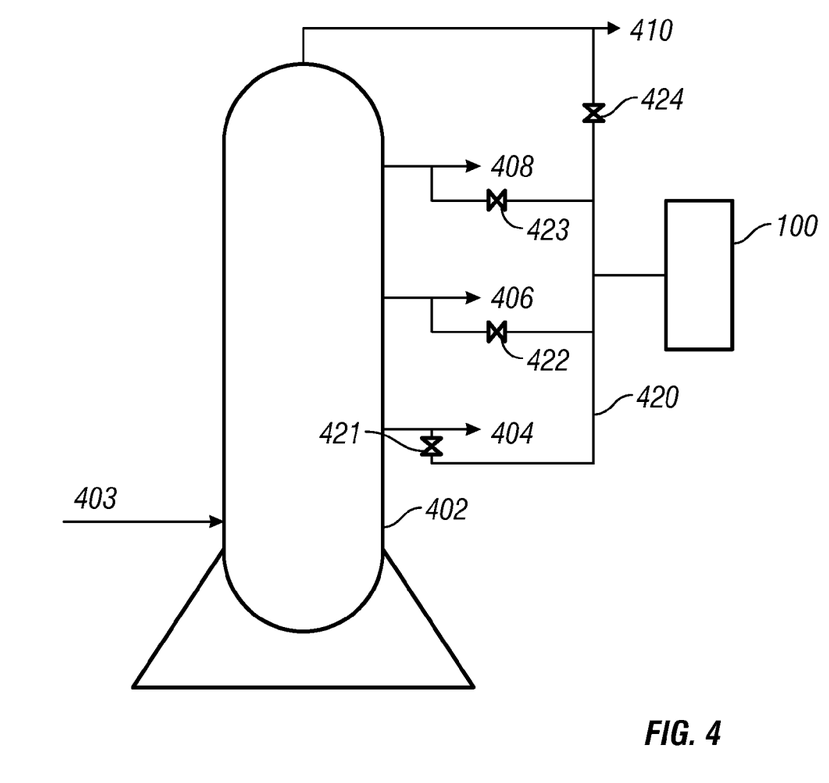
FIG. 4 is a schematic of a fractionating process including a fluid analysis apparatus.

In another example, see FIG. 4, a process feed stream, which may comprise hydrocarbon components, is fractionated in a fractionating apparatus 402. Different fractionating components 404, 406, 408 and 410 are removed at different levels of the process. Samples of fractionating components 404, 406, 408 and 410 may be taken through valves 421, 422, 423 and 424. The samples may be analyzed by an analysis system such as analysis system 100 described previously, or alternatively, by analysis system 200 described previously, to determine the components of the individual streams.

The analysis systems described herein may also be used for analyzing fluid components in pipelines.

In one operational example, for use with a liquid slurry, the length of the energy pulse may be used to control the depth of investigation into the sample, thereby allowing the examination of the carrier liquid while substantially ignoring the slurry solids. In another example, the lengthening of the ON pulse time may be used to detect fouling of the optical windows. For example, a constant acoustic signal amplitude with an increasing ON pulse length, may indicate that the acoustic signal is not penetrating deeper into the sample but is being generated in a substantially small fluid volume near the window.

Numerous variations and modifications will become apparent to those skilled in the art. It is intended that the following claims be interpreted to embrace all such variations and modifications.

What is claimed is:

1. An apparatus for analyzing a fluid comprising:
a single chamber to receive a fluid sample;
a positive displacement pump in hydraulic communication with the single chamber, the positive displacement pump reducing a pressure of the fluid sample in the single chamber below a vapor pressure of a component of the fluid sample;
at least one light system to provide a light at a predetermined modulation frequency to the fluid sample, the light system having a chopper wheel formed with a plurality of rings of slots, each ring modulating the light transmitted to the fluid sample at a different predetermined modulation frequency;
an acoustic sensor to detect an acoustic signal caused by the interaction of the light and the fluid sample;
a controller relating the acoustic signal to at least one chemical component of the fluid sample; and
a plurality of optical filters wherein each optical filter transmits a different predetermined wavelength of light, and wherein each optical filter acts cooperatively with a corresponding ring to transmit light of a predetermined wavelength, $\lambda_i$, at a predetermined modulation frequency, $f_i$, to the fluid sample.

2. The apparatus of claim 1 wherein the light system comprises a broad band light source.

3. The apparatus of claim 1 wherein the light system comprises a light source chosen from the group consisting of a heated filament, a laser, a laser diode, and a tunable laser diode.

4. The apparatus of claim 1 wherein the controller receives a signal at the predetermined modulation frequency generated by the acoustic sensor and relates the signal at the predetermined modulation frequency to a component, Ci, of the fluid sample.

5. The apparatus of claim 1 wherein the acoustic sensor detects at least one acoustic signal associated with at least one of the predetermined modulation frequencies $f_i$, and the controller relates the signal at the at least one detected frequency $f_i$ to a fluid component $C_i$.

6. The apparatus of claim 1 wherein the apparatus is deployed to analyze a fluid sample taken from the group consisting of: a downhole reservoir; a pipeline; and a fractionating apparatus.

7. The apparatus of claim 1 wherein the fluid sample comprises a sample of a reservoir fluid.

8. The apparatus of claim 7 wherein the fluid sample is analyzed at a downhole location in a formation test tool.

9. The apparatus of claim 8 wherein the formation test tool is deployed in a wellbore on at least one of: a wireline; a jointed drill string; a hard wired jointed drill string; and a coiled tubing string.

10. An apparatus for analyzing a formation fluid comprising:
a formation test tool deployed in a wellbore proximate a downhole formation;
a single chamber disposed in the formation test tool to receive a formation fluid sample;
a positive displacement pump in hydraulic communication with the single chamber, the positive displacement pump reducing a pressure of the fluid sample in the single chamber below a vapor pressure of a component of the fluid sample;
at least one light system to provide a modulated light at a predetermined modulation frequency to the fluid sample, the at least one light system having a chopper wheel formed with a plurality of rings of slots, each ring modulating the light transmitted to the fluid sample at a different predetermined modulation frequency;
an acoustic sensor to detect an acoustic signal caused by the interaction of the light and the fluid sample; and
a controller relating the acoustic signal to at least one chemical component of the fluid sample; and
a plurality of optical filters wherein each optical filter transmits a different predetermined wavelength of light, and wherein each optical filter acts cooperatively with a corresponding ring to transmit light of a predetermined wavelength, $\lambda i$, at a predetermined modulation frequency, fi, to the fluid sample.

11. The apparatus of claim 10 wherein the light system comprises a broad band light source.

12. The apparatus of claim 10 wherein the controller receives a signal at the predetermined modulation frequency generated by the acoustic sensor and relates the signal at the predetermined modulation frequency to a component, Ci, of the fluid sample.

13. The apparatus of claim 10 wherein the light system comprises a light source chosen from the group consisting of a heated filament, a laser, a laser diode, and a tunable laser diode.

* * * * *